United States Patent [19]
Camiener

[11] Patent Number: 5,977,153
[45] Date of Patent: Nov. 2, 1999

[54] SOLID ALDEHYDE AND ANTIMICROBIAL COMPOSITIONS USEFUL AS FIXATIVES, PRESERVATIVES AND EMBALMING AGENTS

[76] Inventor: Gerald W. Camiener, 26700 Hurlingham Rd., Beachwood, Ohio 44122

[21] Appl. No.: 08/912,364

[22] Filed: Aug. 18, 1997

Related U.S. Application Data

[63] Continuation of application No. 08/435,130, May 5, 1995, abandoned, which is a continuation-in-part of application No. 08/160,285, Dec. 2, 1993, Pat. No. 5,439,667, which is a continuation of application No. 07/762,307, Sep. 20, 1991, abandoned.

[51] Int. Cl.⁶ .......................... A01N 35/00; A01N 35/02; A01N 43/50; G01N 1/28
[52] U.S. Cl. ......................... 514/392; 514/386; 514/389; 514/390; 514/557; 514/568; 514/574; 514/698; 514/705; 514/711; 514/970; 514/973; 424/75; 424/641; 424/682; 424/DIG. 6; 422/40; 435/40.5
[58] Field of Search ..................... 514/390, 705, 514/392, 386, 389, 557, 568, 574, 698, 711, 970, 973; 422/40; 424/75, 641, 682, DIG. 6; 435/40.5

[56] References Cited

U.S. PATENT DOCUMENTS

| | | | |
|---|---|---|---|
| 2,333,182 | 11/1943 | Jones et al. | 424/75 |
| 2,786,081 | 3/1957 | Kress | 568/601 |
| 3,836,433 | 9/1974 | Wirth et al. | 435/181 |
| 4,136,161 | 1/1979 | Falkowski et al. | 435/5 |
| 4,189,401 | 2/1980 | Louderback | 436/16 |
| 4,207,286 | 6/1980 | Gut Boucher | 422/21 |
| 4,493,821 | 1/1985 | Harrison | 435/40.52 |
| 4,857,300 | 8/1989 | Maksem | 435/40.51 |
| 4,902,613 | 2/1990 | Chang et al. | 435/2 |
| 4,949,669 | 8/1990 | Siegfried et al. | 118/719 |
| 5,001,047 | 3/1991 | Liberman | 435/1.1 |
| 5,196,182 | 3/1993 | Ryan | 424/3 |
| 5,260,048 | 11/1993 | Ryan | 435/40.5 |
| 5,290,706 | 3/1994 | Camiener | 436/174 |
| 5,429,797 | 7/1995 | Camiener | 422/1 |
| 5,460,797 | 10/1995 | Ryan | 435/40.5 |
| 5,488,095 | 1/1996 | Boeckh et al. | 528/361 |
| 5,622,696 | 4/1997 | Camiener | 424/75 |
| 5,849,517 | 12/1998 | Ryan | 435/40.51 |

FOREIGN PATENT DOCUMENTS

| | | |
|---|---|---|
| 3319 564 | 12/1984 | Denmark . |
| 2 048 152 | 3/1971 | France . |
| 51-113811 | 10/1976 | Japan . |
| 2 114 291 | 2/1982 | United Kingdom . |

OTHER PUBLICATIONS

Yanoff et al. The American Journal of Clinical Pathology, vol. 44, No. 2, pp. 167–171 (1963).
Pearse *Histochemistry Theoretical and Applied*, pp. 590–629, Little, Brown & Company (1968).
Hündgen et al. ACTA Histochem., Suppl., vol. 13, pp. 85–93 (1973).
Janigan The Journal of Histochemistry and Cytochemistry, vol. 13, No. 6, pp. 476–483 (1965).
Kinsella, Jr. Spectra–Tint, Biological Stains Speciment Preparation Reagents, (1987).
WPIDS Abstract 80–04466C (1980).
WPIDS Abstract 94–071169 (1994).
WPIDS Abstract 93–197885 (1993).
WPIDS Abstract 80–24364C (1980).
Sabatini, David D. et al., "Cytochemistry and Electron Microscopy," The J. of Cell Biology, vol. 17, pp. 19–58 (1963).

*Primary Examiner*—John Pak
*Attorney, Agent, or Firm*—Foley & Lardner

[57] ABSTRACT

Stable solid forms of preservative and embalming compositions are described which can be prepared by adding a sufficient amount of a chemical or chemicals containing at least one polar group capable of forming hydrogen and Van der Waal bonds with the reactive moieties of the aldehydes and antimicrobial agents in the preservative and embalming compositions. The amount of polar chemical(s) necessary to stabilize the reactive aldehydes and antimicrobial compounds/agents is based on a molar ratio of (i) polar groups in the stabilizing chemicals to (ii) reactive groups in the active preservative ingredient of at least 0.8.

17 Claims, No Drawings

SOLID ALDEHYDE AND ANTIMICROBIAL COMPOSITIONS USEFUL AS FIXATIVES, PRESERVATIVES AND EMBALMING AGENTS

This application is a continuation of application Ser. No. 08/435,130, filed May 5, 1995 now abandoned, which is a continuation-in-part of Ser. No. 08/160,285, filed on Dec. 2, 1993 (now U.S. Pat. No. 5,439,667), which is a continuation of Ser. No. 07/762,307, filed Sep. 20, 1991 (now abandoned).

BACKGROUND OF THE INVENTION

In previous patent applications, the present inventor has reviewed the needs and uses for various safe (non-hazardous) preservative/fixative and embalming/preservative solutions for use in histology, cytology, embalming and anatomic examination procedures. These patents and patent applications include U.S. Pat. No. 5,290,760, U.S. Ser. No. 08/149,820, filed on Nov. 10, 1993, now U.S. Pat. No. 5,429,797, and U.S. Ser. No. 08/160,285, filed on Dec. 2, 1993, now abandoned, the entire specifications of which are incorporated herein by reference. These prior patents and patent applications all relate to solutions for preserving, fixing or embalming biological material.

Also in the group of relatively safe fixative compositions is U.S. Pat. No. 5,196,182 to Streck, which discloses certain antimicrobial compound-based fixative compositions, wherein the active, fixative compound is an antimicrobial compound that is reactive toward biological material. However, the compositions disclosed therein are in liquid form.

The various known aldehyde and antimicrobial agent-based fixative, preservative, and embalming solutions, as well as those disclosed in the patents and applications listed above, all contain one or more aldehyde or antimicrobial agents as the active (reactive) ingredient. The problem with all such solutions, however, is that these fixative, preservative, and embalming chemicals are relatively reactive materials that can easily lose their activity as well as form colored and insoluble polymerized materials when stored in aqueous solutions over time. These chemical reactions generally are oxidative, reductive and polymer-type reactions.

All of these reactive groups are polar in nature, and as such, they tend to be less reactive or non-reactive when stored in a solid anhydrous condition. However, there are two major problems connected with the preparation of anhydrous, solid forms of the types of aldehydes and anti-microbial chemicals that are useful in the compositions described herein.

First, the aldehydes and some of the antimicrobial chemicals described here occur only as liquids or aqueous solutions that cannot be dehydrated and formed into an anhydrous solid. Second, the reactive groups need to be stabilized in order to reduce their reactivity and to permit long-term storage, whether or not the chemicals occur in solid form.

In a few instances, all of the components in such preservative mixtures can be obtained individually in solid anhydrous forms, as is the case with some anti-microbial agent-based compositions. However, even in these few cases where dry powder blends of the mixtures is can be prepared, there is still a need for long-term stabilization of the mixture. The fact that the chemicals may be available in solid form does not does not appear to lessen the need for stabilization when the individual solid components are mixed together.

SUMMARY OF THE INVENTION

There has been a need in the industry for fixative, preservative, and embalming compositions that remain stable over long periods of time. There has been a further need in the industry to provide these stable compositions in solid form in order to facilitate shipping and transport. With these objects in mind, the present inventor undertook to discover how the reactive aldehydes and antimicrobial agents could be prepared and stabilized in anhydrous, solid (including powdered) forms for long-term storage and ease of transport.

The present inventor discovered that stable solid forms of these compositions can be prepared by adding a sufficient amount of a chemical or chemicals containing at least one polar group capable of forming hydrogen and Van der Waal bonds with the reactive mnoieties of the aldehydes and antimicrobial agents. The present inventor further discovered that the amount of polar chemical(s) necessary to stabilize the reactive aldehydes and antimicrobial compounds/agents is based on a molar ratio of (i) polar groups in the stabilizing chemicals to (ii) reactive groups in the active preservative ingredient of at least 0.8. The solid compositions of the present invention are easily formulated into fixative, preservative or embalming solutions by adding water and other ingredients customarily employed in fixative, preservative and embalming solutions.

DETAILED DESCRIPTION OF THE INVENTION

One embodiment of the present invention is a solid or anhydrous composition useful for preparing fixative, preservative or embalming solutions comprising an aldehyde or antimicrobial compound or a combination thereof having at least one reactive group and at least one stabilizing compound containing at least one polar group, wherein the molar ratio of the polar group to the reactive group in the solution is at least about 0.8:1. Preferably, the molar ratio ranges from about 0.8:1 to about 2.0:1. A still more preferred range is from about 1.5:1 to about 2.5:1.

Another embodiment of the present invention is a process for preparing the solid or anhydrous composition comprising the steps of adding a stabilizing compound containing at least one polar group to an aqueous solution comprising an aldehyde or antimicrobial compound or a combination thereof having at least one reactive group and at least one stabilizing compound containing at least one polar group, wherein the molar ratio of the polar group to the reactive group in the solution is at least about 0.8:1, and drying the solution to obtain a solid composition.

The aldehydes having at least one reactive group include, those conventionally used in fixative, preservative and embalming solutions for biological materials. In addition, the aldehydes and include those disclosed in the aldehyde-containing solutions of my co-pending applications U.S. Ser. Nos. 08/149,820 filed on Nov. 10, 1993, now U.S. Pat. No. 5,429,797 and 08/160,285 filed on Dec. 2, 1993, now abandoned, and my U.S. Pat. No. 5,290,760, the entire specifications of which are incorporated herein by reference. Preferred aldehydes are formaldehyde, glyoxal, and dialdehydes having an even number of atoms in the backbone chain separating the two aldehyde groups (hereafter referred to as "even-numbered dialdehydes").

Within the group of even-numbered dialdehydes, the term "backbone chain" as used herein refers to the series of atoms representing the shortest path, i.e., the path containing the fewest atoms, between the two aldehyde groups (as illustrated in the examples below). The number of atoms in the backbone chain is counted beginning with the first backbone atom bonded to either one of the aldehyde groups and then counting to the next covalently bonded backbone atom in the direction of the shortest path until the last atom is reached which is bonded to the second aldehyde group. If the backbone includes a cyclic moiety, then the shortest path between the aldehyde groups is used to determine whether the backbone chain is odd or even.

For example, butane-1,4-dial, which is an even-numbered dialdehyde according to the present invention would be counted as having two backbone atoms:

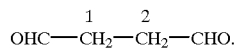
$$OHC-CH_2-CH_2-CHO.$$

Similarly, 4-hydroxymethyl-2,5-diol-1,6-dial-ethylpropyl-ether (a reaction product resulting from a periodic acid reaction on β-D-glucopyranose), which contains an ether backbone, would be counted as follows:

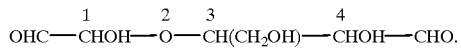
$$OHC-CHOH-O-CH(CH_2OH)-CHOH-CHO.$$

Where the backbone chain involves a ring structure, the atoms which form the shortest path (i.e., which contain the least number of atoms) between the two aldehyde groups are counted. For example, benzene-1,2-dial (a ring dialdehyde) would be even-numbered because there are two carbon atoms which most directly connect the two aldehyde groups. Note that in all cases the hydrogen atoms bonded to the backbone atoms are not counted, since they are not part of the backbone chain, nor are the carbon atoms forming the aldehyde groups counted. Similarly, substituents bonded to atoms of the backbone chain are not counted.

The antimicrobial compounds of the present invention include those conventionally used in antimicrobial-based fixative compositions. For example, the antimicrobial-based preservative and fixative solutions disclosed in U.S. Pat. No. 5,196,182, the entire specification of which is incorporated herein by reference, are suitable. Any antimicrobial compound that is suitable for preservative, fixative or embalming purposes can be used in the present invention which has at least one reactive group that reacts with biological materials. This group of antimicrobial compounds does not include antimicrobials (such as antibiotics) which are effective because of their interference with biochemical and enzyme pathways.

Representative antimicrobial compounds of the present invention having at least one reactive group that reacts with biological material include 2-bromo-2-nitropropane-1,3-diol, quaternary forms of adamantane, sodium azide, dimethylol urea, dimethylol-5,5-dimethylhydantoin, thimerasol imidazolidinyl urea, diazolidinyl urea, 5-bromo-5-nitro-1,3-dioxane, 5-chloro-2-methyl-4-isothiazolin-3-one, 2-methyl-4-isothiazolin-3-one, tetradecyl-trimethyl-ammonium bromide, quaternary ammonium compounds, sodium azide, cacodylic acid and salts thereof, chloroxylenol, phenols, polyphenols, chlorophenols, xylenols, phenoxyethanol, thiopyrroline, sodium hydroxymethyl-glycinate, and glyoxyl-diureide.

The stabilizing compound having at least one polar group can be any such compound provided that it does not react with the aldehyde or antimicrobial compound and provided it is a non-volatile solid at room temperature (about 25° C.). Although the stabilizing compound cannot react with the aldehyde or antimicrobial compound, it will interact with the aldehyde or antimicrobial compound due to hydrogen and van der Waal interactions with the polar group.

All polar group-containing compounds tested as stabilizing compounds have been effective. Preferred stabilizing compounds include at least one polar group selected from the group consisting of alcohol, enol, ketone, carboxyl, sulfhydryl, sulfide, sulfate, sulfonate, phosphate, phosphonate, amine, imine and amide groups.

Only those polar-group containing compounds which are non-volatile solids at room temperature have been found to be effective as stabilizing chemicals. Compounds such as glycerol and ethylene glycol (both volatile at room temperature) were not satisfactory in providing a solid, while polyvinyl alcohol (a non-volatile at room temperature) is suitable. A more preferred group of stabilizing compounds are those compounds containing 2 or more polar groups per molecule, which were very much more effective than mono-functional molecules.

Only non-reactive chemicals (with aldehydes and the antimicrobial compounds), or chemicals that are non-reactive with aldehydes under certain conditions can be used as stabilizers. For example, primary amines at pH 7.0 are very reactive with aldehydes and cannot be used; however, such amines are not reactive at low pH conditions, and at low pH conditions, these amines can be used as stabilizers.

Surprisingly, the present inventor discovered that the effectiveness of stabilizers appears to be related to the molar concentrations of the functional groups, rather than to their ionic strength. For example, equimolar numbers of alcohol and phosphate groups are equally effective as stabilizers, even though phosphate groups markedly increase the ionic strength of the solution.

The minimum amounts of polar groups necessary to achieve satisfactory stabilization is dependent upon the amounts of reactive groups present. The amount of polar groups necessary is expressed as a molar ratio of the molar aiaounts of all of the polar groups present in a mixture divided by the molar amounts of the reactive groups in the mixture. The minimum ratio that has been found to be satisfactory is 0.8 to 1.2.

It is important to note that water is present in most of the compositions prior to drying, and that water is the most polar of all chemicals. Water therefore does function to relieve some of the stabilizer requirement, and this has the effect of lowering the apparent molar ratio. The effectiveness of water varies with the different compounds. In the case of glyoxal, for example, a well-described solid crystalline material is formed when a water solution of glyoxal is dried. No other dialdehyde, nor formaldehyde, is able to form a stable solid material with water alone.

The even-numbered dialdehydes according to the present invention have backbone chains comprising carbon, oxygen, nitrogen and/or sulfur. The backbone chains may be straight, branched, or cyclic. Preferred backbone chains according to the present invention are those containing 2, 4, 6, or 8 atoms. Within this group, preferred backbone chains are those consisting of 2, 4, 6, or 8 carbon atoms. Another group of preferred backbone chains are those containing 2, 4, 6, or 8 atoms, at least one of which is a heteroatom selected from the group consisting of nitrogen, oxygen, and sulfur, and the rest of which are carbon.

Especially preferred even-numbered dialdehydes according to the present invention are those having only carbon in the backbone chain, such as butane-1,4-dial, butane-2,3-diol-1,4-dial, hexane-1,6-dial, octane-1,8-dial, benzene-1,2-dial, and benzene-1,4-dial.

Another preferred group of even-numbered dialdehydes are those containing an ether linkage (an oxygen atom) in the backbone chain. These dialdehydes are formed by periodic acid action on sugar pyranose and furanose compounds.

The even-numbered dialdehydes of the present invention may be used in the form of addition products formed by the reaction of an even-numbered dialdehyde and a reactant selected from the group consisting of bisulfite, water, alcohol, and glycol.

As explained above, the even-numbered dialdehydes of the present invention react in the same way as conventional aldehydes such as formaldehyde and glutaraldehyde, making them useful in a variety of ways. For example, cells and tissues are stabilized when their cell walls, mitochondria, nuclei, and intra-cellular membranes are strengthened and "locked" into place through cross-linking; autolytic decomposition (rotting) is prevented when the autolytic enzymes are inactivated; and microbial decomposition and contagion is prevented through the killing, or inactivation of viruses, bacteria, fungi, and other microbial contagions.

The even-numbered dialdehydes of the present invention may be used in embalming solutions, stabilizing procedures for cells and tissues, histological and cytological reagents, preservation solutions for biological materials, and viral and microbial decontaminating solutions against viruses, fungi, bacteria, and other microorganisms, for use with both biological materials and non-biological materials. Non-biological materials which may be decontaminated according to the present invention include equipment, supplies, instruments, tools, probes, work surfaces, packing supplies, walls, floors, and the like in medical, surgical, food processing, pharmaceutical processing, and other areas where viral and microbial decontamination is important.

Each of these major areas of application will be discussed separately below as they each have their own specific considerations with respect to the even-numbered dialdehydes of the present invention.

Histologic and cytologic fixation procedures require that groups of cells (tissues), the cells themselves, and a wide variety of sub-cellular structures be "locked" spatially in their normal, pre-fixation condition. In order to achieve this effect, the structural components of the cells (comprised primarily of proteins) need to be strengthened and cross-linked to prevent movement, distortion and separation that would otherwise occur during later processing. Also, the tissues and cells need to be protected against decomposition resulting from autolytic enzyme activity and/or microbial decomposition processes.

Solutions destined for use as preservative/fixative and embalming/preservative solutions must effect a broad range of actions in addition to their aldehyde effects. These include osmotic control, pH buffering, penetration, dye mordanting, coloring, antimicrobial action, and the like. In this context, the present inventor has found polyfunctional organic acids to be the most effective compounds in providing satisfactory stabilization. These acids include chemicals like citrates, oxalates, glycolates, alkane sulfonates, indicator sulfonates, and salicylates.

The term "drying" as used herein to prepare solid or powdered compositions from a solution refers to processes known in the art wherein a concentrated aqueous solution is heated above room temperature under vacuum conditions. Although less strong conditions can sometimes be used, drying times are increased substantially and solid products may not be formed. Therefore, it is preferred to heat the concentrated solutions to a temperature above room temperature in order to form a liquid that will solidify upon cooling, and which then can be broken up or powdered. A preferred temperature range is from about 45° to about 150° C., and an even more preferred range is from about 60° to about 100° C.

In addition, standard spray drying techniques known in the art, which apparently form a powder directly without the appearance of a liquid, can also be used in the present invention.

The stabilized, anhydrous solid compositions of the present invention have been found to possess the following properties and characteristics:

1. They were stable at temperatures at least as high as 4° C. (the highest tested) with no detectable loss of reactive group content after more than 1 year, when the concentrations of the reactive groups ranged from about 0.08% by weight of the solid/powdered preparation and higher.
2. They were able to release the reactive group in preservative/fixative and embalming/preservative effective-amounts when contacted with aqueous liquids comprised of water alone, or with water containing standard chemicals employed in fixative, preservative, and embalming compositions including:
   a. from about 0.1 to about 14%, by weight of an osmotic controlling ionic or nonionic chemical or combination of such chemicals;
   b. from about 0.15 to about 60% by volume of a $C_{1-4}$ alkane mono-, di- or triol;
   c. from about 0.3% to about 75% by volume of an acid selected from the group consisting of formic, acetic, hydrochloric, citric and nitric acids, their alkali-metal salts, their ammonium salts, and combinations thereof;
   d. from about 0.1% to about 18% by weight of a chelating agent;
   e. from about 0.1% to about 10% by weight of the mordant-effective-metal-salts of zinc and aluminum;
   f. from about 0.1% to 20% by weight of buffering effective compounds discussed and also described later as stabilizing compounds (buffer compounds often are effective in buffering against pH changes by virtue of the same reactive groups that also are inter-active for stabilization during drying;
   g. from about 0.01% to about 5%, by weight, of a dye that (i) color biological tissues in a manner such that said tissue can be readily identified from among other contents of said aqueous medium; and (ii) does not interfere with the subsequent processing of said tissue;
   h. or a mixture of 2 or more components described in items 2a through 2g, immediately above.
3. They were unaffected by the presence, during the drying steps and during the storage, of a wide variety of additional chemical compounds, at even quite high concentrations, as measured by the release of the aldehyde or other reactive group content preservative/fixative (for histology and cytology) and embalming/preservative (for storage and anatomic examination of bodies and parts thereof) forms and concentrations when contacted with aqueous liquids as described in item 2, above. Such additions included:
   a. Aldehydes in the form of bisulfite, hydrate and alcohol addition products;
   b. Osmotic controlling ionic or nonionic chemicals, or combinations thereof, in concentrations ranging from about 0.1 to about 65%, by weight, of the final solid form;
   c. Buffering (pH) chemicals, as discussed in Item 2f, above, and later in this report, in amounts ranging from about 0.1% to about 80%, by weight of the final solid form;

d. Chelating chemicals in amounts from about 0.1% to about 65%, by weight, of the final solid form. Chelating chemicals, like buffers, are effective by virtue of having reactive groups that also are inter-active for stabilization during drying;

e. Antimicrobial chemicals, in amounts from about 0.15% to about 62%, by weight, of the final solid form;

f. Mordant-effective metal salts of zinc and aluminum, in amounts from about 0.10% to about 10%, by weight, of the final solid form;

g. Biological dyes, as described in item 2h, above, from about 0.02% to about 9.0% of the final solid form;

h. Antimicrobial chemicals, in amounts from about 0.15% to about 62%, by weight, of the final solid form;

i. Or a mixture of 2 or more of the components described in items 3a through 3h immediately above.

4. The reactive compounds considered for use in the preservative/fixative and embalming/preservative applications are of two types:

a. Aldehydes selected from the group of formaldehyde and even-numbered dialdehydes defined herein;

b. Antimicrobial chemicals that are selected from the group that are effective as antimicrobials because of their chemical reactivity toward biological materials, as opposes to those chemicals (like antibiotics) which are effective because of their interference with biochemical and enzyme pathways. Such chemically reactive anti-microbial chemicals include chemicals like 2-bromo-2-nitropropane-1,3-diol, quaternary forms of adamantane, sodium azide, dimethylol urea, dimethylol-5,5-dimethylhydantoin, thimerasol imidazolidinyl urea, diazolidinyl urea, 5-bromo-5-nitro-1,3-dioxane, 5-chloro-2-methyl-4-isothiazolin-3-one, 2-methyl-4-isothiazolin-3-one, tetradecyl-trimethyl-ammonium bromide, quaternary ammonium compounds, sodium azide, cacodylic acid and salts thereof, chloroxylenol, phenols, polyphenols, chlorophenols, xylenols, phenoxy-ethanol, thiopyrroline, sodium hydroxymethyl-glycinate, and glyoxyl-diureide.

Biological materials which may be preserved with solutions prepared from the solid compositions of the present invention include biological materials from human, non-human animal, and plant sources. In particular, such materials include cells, tissues, organs, organisms, whole bodies, parasites, parasite eggs, blood, urine, and fecal samples.

When preparing solutions comprising the solid compositions of the present invention, other ingredients may be added including osmotic controlling chemicals, alcohols, buffering agents, and divalent, trivalent or transition metal salts. Also, when preparing embalming solutions, conventional ingredients may be employed such as chemicals that provide humectant properties, suppleness of the tissue, coloration, bleaching, and outlining of vascular structures.

Osmotic controlling chemicals include potassium chloride, potassium bromide, lithium bromide, lithium chloride, calcium chloride, calcium phosphate, magnesium chloride, magnesium sulfate, sodium phosphate, potassium phosphate, sodium chloride, sodium bromide, sodium sulfate, sucrose, mannitol, trehalose, polyvinyl alcohol, and polyvinyl pyrrolidone. Such chemicals are used preferably at osmotically-compatible concentrations, either alone or in combination with each other.

Alcohols include mono-, di-, and triols such as methyl alcohol, ethyl alcohol, isopropyl alcohol, ethylene glycol, propylene glycol, glycerol. Preferably, such alcohols are added to the preservative solutions at concentrations ranging from 0.4% to 32% by volume, but some preservative and embalming solutions may include up to 90% by volume.

Buffering agents include citrate buffer, acetate buffer, phosphate buffer, and 2-N-morpholinoethane-sulfonate buffer at pH values ranging from pH 3.0 to pH 7.8.

Bivalent and trivalent metal and transition metal salts include salt forms of zinc, aluminum, calcium, magnesium and iron.

Other ingredients include antimicrobial agents, germicides, virucides, decalcifying agents (such as formic, hydrochloric, citric, and nitric acids, and/or their alkali metal or ammonium salt forms), or chelating agents (such as EDTA and its alkali metal or ammonium salts), all of which are used in a conventional manner in fixative solutions.

Preferred amounts of the above-identified compounds in the compositions of the present invention and solutions prepared from them are as follows. A preferred amount of the aldehyde(s) in the solid compositions is from about 0.08% to about 80%, by weight of the overall composition. The aldehyde compound(s) may optionally be in the form of a bisulfite, hydrate, or alcohol addition product. A preferred amount of the reactive anti-microbial compound is from about 0.15% to about 62.0%, by weight of the composition. A preferred amount of the osmotic-controlling chemical is from about 0.1% to about 65%, by weight of the composition. A preferred amount of the buffering agent is from about 0.1% to about 80%, by weight which is sufficient to maintain the pH when the composition is contacted with said aqueous liquid.

Optionally, the composition may further contain from about 0.1% to about 65%, by weight, of a chelating compound.

A preferred amount of the alcohol(s) is from about 0.15% to about 36%, by volume, of the aqueous liquid to which the solid composition is added.

A preferred amount of the acid is from about 0.30% to about 75%, by volume, of the aqueous liquid to which the solid composition is added.

In addition, the compositions may further contain from about 0.02% to 10.0%, by weight of a dye that (i) colors biological tissue in a manner such that said tissue can be readily identified from among other contents of an aqueous medium; and (ii) does not interfere with subsequent processing of said tissue.

A preferred amount of the heavy metal salt(s) is from about 0.10% to about 10.0% of a mordant-effective metal salt or combination of salts, e.g., zinc and aluminum.

The present invention is further illustrated by, though in no way limited to, the following examples:

EXAMPLE 1

A test solution was prepared by mixing 100 ml of 1.0 M citric acid, pH 3.5 with 100 ml of a 40% glyoxal solution. The solution was evaporated on a RotoVap evaporator rotating at 20 revolutions per minute in an 80° C. water bath under a vacuum of <5 microns. After 2 hours, the solution was cooled and it solidified into a solid mass, which subsequently was powdered and stored at room temperature. After more than 2½ years of storage, the powder was tested for content of reactive groups and fixative activity after being contacted with deionized water. The reactive group content and fixative activity was found to be unchanged, within experimental error, as compared to a fresh control.

EXAMPLE 2

A test solution was prepared using citric, alkane-sulfonic, glycolic and salicylic acids plus butanedialdehyde at a molar ratio of 1.0. The material was spray-dried in a commercial-type spray drier with an incoming air temperature of 60° C. A fine white powder was obtained. After more than 4 months storage at 40° C., the powder was tested as in Example 1. No loss in activity or aldehyde content was observed.

EXAMPLE 3

A test solution was prepared using citric, alkane-sulfonic, glycolic, and salicylic acids plus diazolidinyl urea at a molar ratio of 1.8. The material was evaporated as in Example 1. After 4 months of storage at room temperature, the powder was tested for content of reactive groups and fixative activity after being contacted with deionized water. The reactive group content and fixative activity was found to be unchanged, within experimental error, as compared to a fresh control.

EXAMPLE 4

A dry powder blend of the components in Example 3 was prepared in a Fitz Mill to provide uniform size and intimate mixing. The acid portions of the mix consisted of the free acids and their sodium salts in relative amounts such that the pH of an aqueous solution prepared with them was pH 5.5. The results were the same as in Example 3.

Comparative Tests

In the reverse direction, it should be noted that when drying attempts are made with insufficient amounts of stabilizing chemicals present in the aqueous solution, the results are not satisfactory. When such drying is performed at lower temperatures (as for example in lyophilization), the solution appears to retain some tightly-bound water and remains liquid even after days of drying. At higher temperatures (as for example 200° C.), where the tightly bound water can be removed, the reactive chemicals are not stabilized, and they degrade to form dark-colored insoluble products. Thus, without the discovery of the present inventor that a molar ratio is required of (i) polar groups in the stabilizing chemicals to (ii) reactive groups in the active preservative ingredient of at least 0.8, it would not have been possible to prepare solid aldehyde and antimicrobial-based preservative and embalming compositions using standard drying techniques.

What is claimed is:

1. A solid or powdered preservative/fixative composition comprising:
   (a) a preservative-, fixative-, or embalming-effective amount of an agent having at least one reactive group selected from the group consisting of butanedialdehyde and diazolidinyl urea; and
   (b) an effective stabilizing amount of at least one compound having at least one polar group selected from the group consisting of citric acid, alkane sulfonic acid, glycolic acid, salicylic acid or a salt thereof;
   wherein the molar ratio of reactive group(s) of any preservative, fixative or embalming ingredient in the composition to polar group(s) of any other ingredient in the composition is at least 0.8 to 1;
   wherein said ingredients are released in an active form when said composition is contacted with an aqueous liquid, resulting in a solution that is suitable for preserving, fixing, or embalming biological materials.

2. The composition as claimed in claim 1 wherein said composition further comprises from about 0.1 to about 65%, by weight, of an osmotic controlling ionic or nonionic chemical, or a combination of osmotic controlling ionic or nonionic chemicals in an amount sufficient to provide osmotically-effective concentrations after contacting said aqueous liquid.

3. The composition as claimed in claim 1, wherein the composition further comprises an effective amount of at least one buffering agent in an amount ranging from 0.1% to about 80%, by weight, for maintaining the pH when the composition is contacted with said aqueous liquid.

4. The composition as claimed in claim 1 wherein said composition further comprises from about 0.1% to about 65%, by weight, of a chelating compound.

5. The composition as claimed in claim 1 wherein said composition further comprises from about 0.02% to about 10.0%, by weight of a dye that (i) colors biological tissue to permit said tissue to be readily identified from among other contents of an aqueous medium; and (ii) does not interfere with subsequent processing of said tissue.

6. The composition as claimed in claim 1 wherein said composition further comprises from about 0.10% to about 10.0% by weight of a mordant-effective metal salt of zinc or aluminum or combination of salts of zinc and aluminum.

7. The composition as claimed in claim 1, wherein (a) is diazolidinyl urea and (b) is a mixture of citric, alkane-sulfonic, glycolic, and salicylic acids in free acid and sodium salt form.

8. The composition of claim 1, wherein said molar ratio is from 1.5:1 to 2.5:1.

9. A process for preserving, fixing or stabilizing biological material for microscopic examination which comprises adding an aqueous liquid to a solid or powdered composition comprising:
   (a) a preservative- or fixative-effective amount of an agent having at least one reactive group selected from the group consisting of glyoxal, butanedialde, and diazolidinyl urea; and
   (b) an effective stabilizing amount of at least one compound having at least one polar group selected from the group consisting of citric acid, alkane sulfonic acid, glycolic acid, salicylic acid or a salt thereof;
   wherein the molar ratio of reactive group(s) of any preservative or fixative ingredient in the composition to polar group(s) of any other ingredient in the composition is at least 0.8 to 7.
   thereby producing a solution wherein said ingredients of the solid or powdered composition are released in an active form suitable for preserving, fixing, and stabilizing biological material for microscopic examination; and contacting a biological material with said solution to render the biological material suitable for microscopic examination.

10. The process as claimed in claim 9 wherein said composition further comprises from about 0.1 to about 65%, by weight, of an osmotic controlling ionic or nonionic chemical, or a combination of osmotic controlling ionic or nonionic chemicals in an amount sufficient to provide osmotically-stabilizing effective concentrations after adding the aqueous liquid.

11. The process as claimed in claim 9 wherein the composition further comprises an effective amount of at least one buffering agent in an amount ranging from 0.1% to about 80%, by weight, for maintaining the pH when the composition is contacted with said aqueous liquid.

12. The process as claimed in claim 9 wherein said composition further comprises from about 0.1% to about 65%, by weight, of a chelating compound.

13. The process as claimed in claim 9 wherein said aqueous liquid further comprises from about 0.15% to about 36%, by volume, of a $C_{1-4}$ alkane mono-, di-, or triol.

14. The process as claimed in claim 9 wherein said aqueous liquid further comprises from about 0.3% to about 75%, by volume, of an acid selected from the group consisting of formic, hydrochloric, acetic, citric, and nitric acids, their alkali metal salts, their ammonium salts, and combinations thereof.

15. The process as claimed in claim 9 wherein said composition further comprises from about 0.02% to 10.0%, by weight of a dye that (i) colors biological tissue to permit said tissue can be readily identified from among other contents of an aqueous medium; and (ii) does not interfere with subsequent processing of said tissue.

16. The process as claimed in claim 9 wherein said composition further comprises from about 0.10% to about 10.0% by weight of a mordant-effective metal salt of zinc or aluminum or a combination of salts of zinc and aluminum.

17. The process of claim 9, wherein said molar ratio is from 1.5:1 to 2.5:1.

* * * * *